United States Patent [19]

Marx

[11] Patent Number: 5,662,631
[45] Date of Patent: Sep. 2, 1997

[54] MALE EXTERNAL CATHETER ASSEMBLY WITH VACUUM RETENTION

[76] Inventor: Sherwood D. Marx, 6478 S. M, Tacoma, Wash. 98408

[21] Appl. No.: 689,765

[22] Filed: Aug. 13, 1996

[51] Int. Cl.[6] .................................................. A61F 5/44
[52] U.S. Cl. .............................................. 604/352; 604/349
[58] Field of Search ................................... 604/349, 351, 604/352, 327, 355

[56] References Cited

U.S. PATENT DOCUMENTS

| | | |
|---|---|---|
| 4,475,910 | 10/1984 | Conway et al. . |
| 4,997,427 | 3/1991 | Bowen . |
| 5,013,308 | 5/1991 | Sullivan . |
| 5,059,190 | 10/1991 | Novak . |
| 5,211,640 | 5/1993 | Wendler . |
| 5,499,977 | 3/1996 | Marx . |

*Primary Examiner*—Robert A. Clarke
*Attorney, Agent, or Firm*—Graybeal Jackson Haley LLP

[57] ABSTRACT

A male external catheter attachment assembly incorporating vacuum or reduced pressure producing means to aid in installation and retention of the assembly in place. Reduced pressure is applied interiorly within a rigid catheter sleeve and a thin elastomeric sheath which in turn covers and applies the reduced pressure to the penis of the wearer while such is maintained within the catheter sleeve both during installation and during use. An optional centering ring surrounds an intermediate portion of the sheath. Optionally, also, the vacuum or reduced pressure producing means can in valved communication with the interior of the catheter sleeve outlet and the drainage tube, and can be removable from the assembly when not in use.

15 Claims, 1 Drawing Sheet

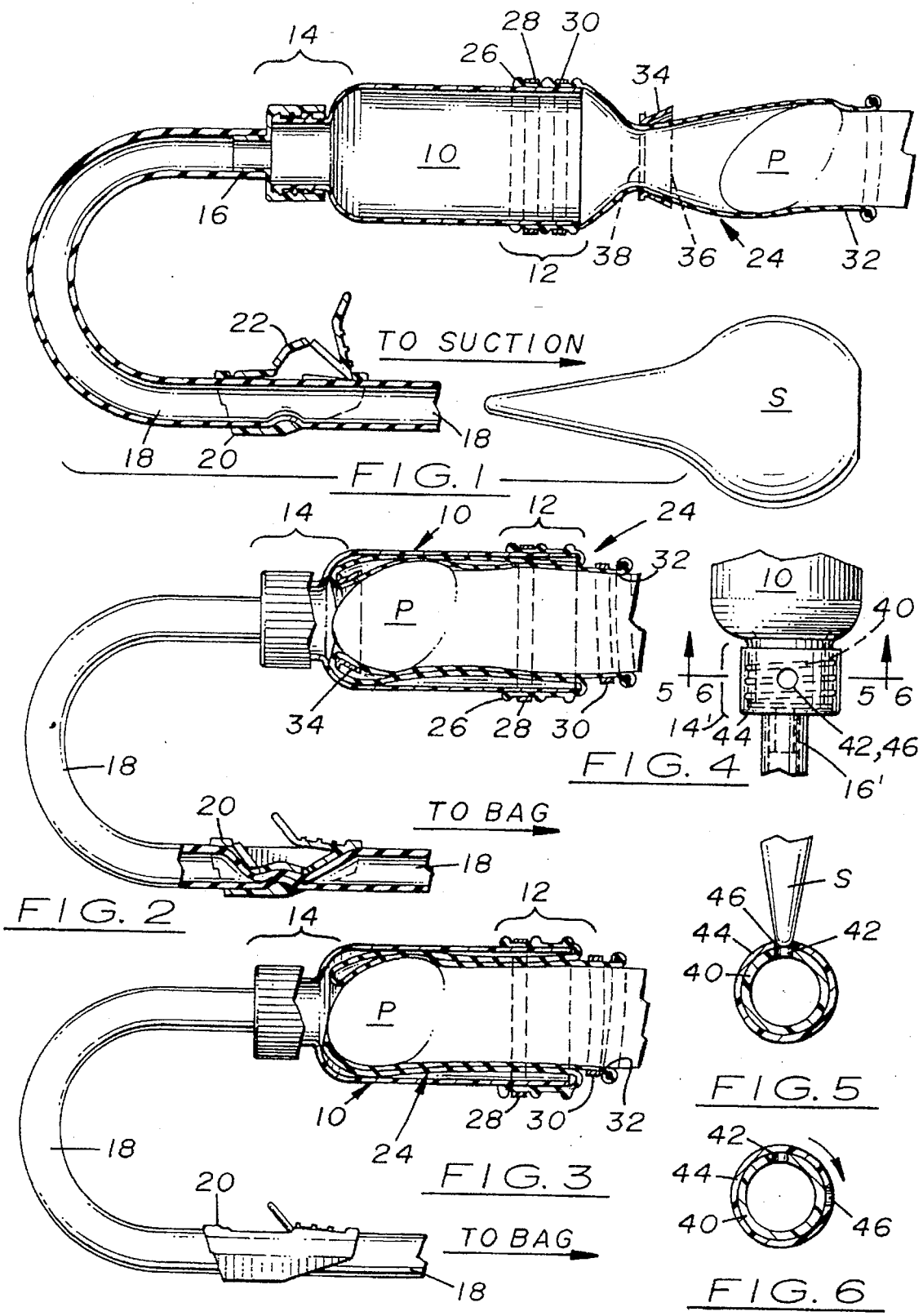

5,662,631

MALE EXTERNAL CATHETER ASSEMBLY WITH VACUUM RETENTION

BACKGROUND OF THE INVENTION

1. Field of the Invention

The present invention relates to male urinary incontinence devices and more particularly to male external catheters and catheter attachment assemblies utilizing vacuum to aid in installation and retention of the assembly in place on the male patient.

2. Description of the Prior Art

Urination incontinence devices with external catheters, also called urisheaths, are well known and also have well known problems making them complicated, difficult, uncomfortable and generally unreliable from the point of view of persons having to use them. One chronic problem is that of keeping the catheter in place on the penis of the user, for which some of such incontinence devices utilize adhesive interiorly of the catheter. Typical of such usage are the devices disclosed in U.S. Pat. Nos. 4,475,910, 5,211,640 and 5,059,190. Similarly, the devices disclosed in U.S. Pat. Nos. 4,997,427 and 5,013,308, utilize relatively complicated body engaging parts which are attached to the male patient's body by adhesive means or belts, to attempt to retain the penis surrounding portion of the assembly in place during use.

Also known is applicant's prior U.S. Pat. No. 5,499,977 which utilizes vacuum in a manner assisting the installation of the catheter assembly onto the user's penis. More specifically, in applicant's earlier external catheter assembly a rolled up elastomeric ring is arranged on the end of a catheter of generally tubular form and engages the end of the male organ, with vacuum being applied at the other end of the tubular form and within the tubular form to firmly hold the tubular form against the penis while rolled the elastomeric ring is unrolled onto the penis. With the catheter tube thus installed the portion of the assembly generating the vacuum during installation of the catheter on the penis is removed and the catheter is then connected to a drainage tube which leads to a urine collection bag. With this assembly, although a vacuum is used to aid in installation of the catheter tube onto the patient male organ, the continuing retention of the catheter tube on the penis is simply by the mechanical interaction between the unrolled elastomeric ring and the surface of the penis and can in some instances be insufficient to avoid leakage or detachment of the catheter.

SUMMARY OF THE INVENTION

As an object and feature of the present invention to provide a catheter attachment assembly for use on the penis of a male patient which utilizes vacuum to both aid in the installation of the catheter onto the penis and in the retention of the catheter in place during use without leakage and discomfort.

It is a further object and feature of the present invention to provide an external catheter attachment assembly which is effective in maintaining the attachment in place on the penis of a male patient without use of adhesive or tape or straps or fasteners of any kind, and with only a very small portion of the penis getting wet during use.

A further advantage and feature of the catheter assembly of the present invention is that it is extremely easy to use and comfortable in use.

It is yet another object and feature of catheters according to the invention is that all parts thereof can be either clear plastic or translucent so that the parts can be observed interiorly while the assembly is being installed on the patient.

These and other objects, features and advantages of catheter attachments and assemblies according to the present invention will be realized and understood by those skilled in the art to which the invention is addressed, giving due consideration to the disclosure of certain typical embodiments thereof as shown and described in the accompanying drawings and following description.

BRIEF DESCRIPTION OF THE DRAWINGS

FIG. 1 is a view in partial cross-section and in side elevation of the components of an external catheter assembly according to the present invention, shown in association with the penis of a male patient at the start of the installation of the catheter onto the male organ;

FIG. 2 is a view in partial cross-section and in side elevation of the catheter attachment assembly shown in FIG. 1, with the parts thereof in their relative positions with the assembly fully installed on the male organ; and FIG. 3 is a view partially in cross-section and in side elevation of a somewhat modified form of external catheter assembly, shown it fully installed in like manner as the assembly shown in FIG. 2, but without a centering ring arranged in surrounding relation to the intermediate portion of the elastomeric sheath.

FIGS. 4, 5 and 6 are detailed views of a further modified form of assembly according to the invention, involving a radial hole in the distal end of the catheter sleeve and a threaded screw cap with a radial hole which in one position aligns with the radial hole in the sleeve and establishes fluid flow communication into the catheter and drainage tube for application of suction therethrough by a vacuum producing component and which in another position of the screw cap closes off such communication to retain the reduced pressure within the sleeve.

DESCRIPTION OF THE PREFERRED EMBODIMENTS

The catheter attachment assembly is shown in FIG. 1 in conjunction with a portion of a male patient's penis P and a conventional suction or vacuum applying device in the form of a syringe S, which is suitably of a type which is conventional per se. The assembly components comprise a rigid, clear plastic, generally cylindrical catheter sleeve 10 having an open proximal end 12 and reduced diameter distal end 14 with distally converging surfaces and a reduced diameter coupler or coupling means 16 which is part of and interconnects said catheter sleeve distal end to a drainage tube 18 in turn leading to a urine collection bag (not shown) in a manner conventional per se. Coupler means 16 comprises a threaded interconnection with the sleeve distal end 14 for ready removal of the coupler means 16 from the sleeve 10 when the wearer needs to urinate.

Manually actuatable closure means 20 is located on drainage tube 18 and has a movable component 22 which in one position provides that the drainage tube 18 is open for fluid flow therethrough (as in FIG. 1) and which in another position completely closes off the drainage tube 18 (as in FIG. 2), as will be evident, closure means 20 in effect functions as a valve means in the tube 18 in that it functions to open or close the tube 18, as desires.

The catheter attachment assembly shown in FIGS. 1 and 2 further comprises a thin elastic open-ended sheath, generally indicated at 24, which has a nominal cross-sectional diameter throughout somewhat less than that of the catheter sleeve 10. Distal end 26 of sheath 24 is attached in an airtight manner to the open proximal end 12 of the catheter sleeve 10. In the preferred form of the assembly shown in FIG. 1, such attachment is by two elastic band means 28, 30 providing an airtight seal between the sleeve 10 and the sheath 24. Sheath 24 further comprises an open proximal end 32 which in nominal form before unpackaging and before any application of the assembly to the penis P can be partially rolled up and in turn then unrolled onto a portion of the penis P as the first step of installation of the assembly for use, substantially as shown in FIG. 1. As will be apparent, the sheath 24 suitably can be a conventional condom with its closed end cut off so that the sheath 24 is open at both its distal end 26 and its proximal end 32.

In the form shown in FIG. 1, the catheter attachment assembly further comprises a centering ring 34 of a smaller diameter than the diameter of the sleeve 10 which is arranged in surrounding relation to the sheath 24 intermediately of the ends of said sheath 24. The centering ring 34 serves to aid in the centering of the distal end of the penis P within the sleeve 10 as the penis P is drawn within the sleeve 10 in the course of installation of the penis within the sleeve 10 under vacuum as discussed below in connection with FIG. 2. As shown in said FIG. 1, the proximal edge 36 of the ring 34 is somewhat larger than the distal edge 38 thereof.

FIG. 2 illustrates the component arrangement of the catheter attachment assembly shown in FIG. 1 with the assembly fully installed on the penis P of a male patient. Preliminary to installation of the catheter assembly on the user, it has been found advantageous to apply dry powder such as talcum powder to the parts in the course of placement on the wearer. Then, to effect such installation, and referring again to the component parts in their relation as shown in FIG. 1, vacuum is applied through application of suction device S to the drainage tube 18 and through the closure means 20 in its open condition, then through coupling means 16 to the interior of the sleeve 10 and consequently the interior region of the sheath 24. As a result of the force of the external air pressure resulting from the applied suction, the penis P is drawn into closer engagement with and through the sheath 24, and against the centering ring 34, moving progressively into the sleeve 10 until the ring 34 and distal end of the penis P seat against the interior face of the sleeve 10 distal end 14 as shown in FIG. 2. When the penis reaches such position, the closure means 20 is manually actuated to close off the drainage tube 18, the suction device S is removed from the drainage tube 18 and the tube 18 connected to the urine collection bag (not shown), the collection bag in the meanwhile having been collapsed to the point of removal of all available air therefrom. With the collapsed bag connected to the tube 18, the closure means 20 is then reopened permitting eventual discharge of any urine accumulated by the catheter assembly through the drainage tube 18 into the urine collection bag. As will be noted, the penis in such condition is retained in the catheter sleeve 10 on a continuing basis, and at least in part by the continuing vacuum condition existing within the catheter sleeve 10. If necessary, to aid in retention of the sheath 24 on the penis P, one of the elastic band means 30 can be moved off the proximal end 12 of the sleeve 10 and onto the penis P in encircling and sealing engagement with the sheath 24 end 32, as shown in FIG. 2.

FIGS. 4, 5 and 6 show in partial detail a portion of a further modified form of catheter attachment assembly according to the present invention, wherein the distal end 14' of the catheter sleeve has an external surface 40 in the configuration of a male thread and a radially directed throughhole 42, with the drainage tube coupler means 16' comprising a screw cap 44 with a radially directed throughhole 46 which in one rotational position of the screw cap 44 is in radial alignment with the throughhole 42, as shown in FIG. 5. As will be understood, with such throughholes 42, 44 in radial alignment, the interior of the catheter sleeve distal end 14' and the interior of the drainage tube 18 are in fluid communication with the exterior through such throughholes 42, 46 and application of a vacuum producing component such as syringe S to said throughhole 46, and application of suction thereby, causes reduced pressure distally in the catheter sleeve 10 and in the drainage tube 18. Then, with suction continuing to be applied, a suitable partial turn, such as a quarter turn, of the screw cap 44 on the threads 40, as shown in FIG. 6, closes off such fluid communication path and in effect sustains the reduced pressure within the distal end of the catheter sleeve 10 and in the drainage tube 18. As will be evident, the catheter sleeve distal end 14' with its threaded surface 40 and throughhole 42, and screw cap 44 with its through hole 46, function as a manually actuatable valve means in that they function to provide manually actuatable valvular communication of selectively usable pressure reducing means interiorly of the catheter sleeve outlet and the drainage tube of the catheter assembly. As will also be apparent, this arrangement provides a very simple procedure by which a user can reestablish reduced pressure retention of the catheter assembly on the wearer's penis after the nominal interruption of reduced pressure within the catheter sleeve, for whatever reason. It also provides a readily available way in which a user or a medical attendant can increase the amount of vacuum present without any disassembly of the apparatus.

Of the foregoing, various further modifications, and adaptations and arrangements of components characteristic of the invention will occur to those skilled in the art to which the invention is addressed, within the scope of the following claims.

What is claimed is:

1. An external catheter attachment assembly for use on the penis of a male patient without concern as to leakage or discomfort, said catheter attachment assembly being characterized by use of vacuum to aid in installation and retention of the assembly in place on the male patient and comprising:

a catheter sleeve with an open proximal end and a reduced diameter distal end including means for coupling said distal end to a drainage tube;

a drainage tube in fluid communication with the interior of the distal end of said sleeve;

manually actuatable valve means in communication with the interior of the distal end of said sleeve and the drainage tube;

a thin elastic open-ended sheath having a nominal cross-sectional diameter throughout which is somewhat less than that of said sleeve, with a distal end attached in an airtight manner to the open proximal end of said sleeve and with an open proximal end installable on the penis of the male patient; and means including said valve means for selectively applying a vacuum to the interior of said sleeve and the interior portion of said sheath in open communication with said interior of said sleeve;

said catheter attachment assembly being installable on the penis of the male patient by installing said elastic sheath proximal end on the penis, then applying vacuum interiorly of the sleeve to draw the penis and a portion of said sheath into said sleeve under the force of the external air pressure resulting from the applied vacuum and bring the distal end of the user's penis substantially into engagement with the interior of said sleeve at the distal end thereof, then utilizing said valve means to close off further application of vacuum to retain the penis in the catheter sleeve on a continuing basis at least in part by the continuing reduced pressure condition existing within said catheter sleeve.

2. The attachment assembly of claim 1, wherein said manually actuatable valve means applying vacuum to the interior of said sleeve is connected to apply same interiorly of said drainage tube.

3. The attachment assembly of claim 1, wherein said valve means comprises fluid flow holes in the distal end of said sleeve and in a rotatable screw cap which are alignable to enable application of vacuum through said holes to the interior of the catheter sleeve distal end and to close off such communication by relative rotation of said screw cap.

4. The attachment assembly according to claim 1, wherein elastic band means overlies said sheath distal end and the proximal end of said catheter sleeve.

5. The attachment assembly of claim 4, comprising two elastic band means, one of which is movable from encircling engagement with said sheath and said sleeve to a position nearer the proximal end of said sheath and in a position encircling the penis of the male patient to aid in retention of the sheath on the penis and aid in maintenance of a continuing vacuum condition in said sleeve during use of the assembly.

6. The attachment assembly of claim 1, further comprising a centering ring with a smaller diameter than the diameter of said catheter sleeve and arranged in surrounding relation to said sheath intermediately of the ends of said sheath, said centering ring serving to center the end of the penis within said sleeve as the penis is drawn within the sleeve under vacuum.

7. The attachment assembly of claim 1, wherein said catheter sleeve is generally cylindrical form.

8. The attachment assembly of claim 7, wherein said catheter sleeve comprises a clear plastic wall.

9. An external catheter attachment assembly for use on the penis of a male patient without concern as to leakage or discomfort, said catheter attachment assembly being characterized by use of vacuum to aid in installation and retention of the assembly in place on the male patient and comprising:

a generally cylindrical catheter sleeve with an open proximal end and a reduced diameter distal end including means for coupling said distal end to a drainage tube;

a drainage tube in fluid communication with the interior of the distal end of said sleeve;

a thin elastic open-ended sheath having a nominal cross-sectional diameter throughout which is somewhat less than that of said sleeve, with a distal end attached in an airtight manner to the open proximal end of said sleeve and with an open proximal end installable on the penis of the male patient; and means including manually actuatable valve means openable to selectively apply a vacuum to said drainage tube and to the interior of said sleeve and the interior portion of said sheath in open communication with said interior of said sleeve and closable to retain reduced pressure in such tube and interior portions;

said catheter attachment assembly being installable on the penis of the male patient by installing said elastic sheath proximal end on the penis, then applying vacuum interiorly of the sleeve through said valve means to draw the penis and a portion of said sheath within said sleeve under the force of the external air pressure resulting from the applied vacuum, then closing said valve means, with the penis being retained in the catheter sleeve on a continuing basis at least in part by the continuing reduced pressure condition existing within said catheter sleeve.

10. The attachment assembly of claim 9, wherein said manually actuatable valve means applying vacuum to the interior of said sleeve is connected to apply same interiorly of said drainage tube.

11. The attachment assembly of claim 9, wherein said valve means comprises fluid flow holes in the distal end of said sleeve and in a rotatable screw cap which are alignable to enable application of vacuum through said holes to the interior of the catheter sleeve distal end and to close off such communication by relative rotation of said screw cap.

12. The attachment assembly according to claim 9, wherein said sheath distal end is in overlying engagement with the proximal end of said catheter sleeve.

13. The attachment assembly of claim 12, comprising elastic band means encircling the distal end of said sheath and the proximal end of said sleeve.

14. The attachment assembly of claim 13, comprising two elastic band means, one of which is movable from encircling engagement with said sheath and said sleeve to a position nearer the proximal end of said sheath and in a position encircling the penis of the male patient to aid in retention of the sheath on the penis and aid in maintenance of a continuing vacuum condition in said sleeve during use of the assembly.

15. The attachment assembly of claim 9, further comprising a centering ring with a smaller diameter than the diameter of said catheter sleeve and arranged in surrounding relation to said sheath intermediately of the ends of said sheath, said centering ring serving to center the end of the penis within said sleeve as the penis is drawn within the sleeve under vacuum.

* * * * *